(12) United States Patent
Furst et al.

(10) Patent No.: US 7,648,590 B2
(45) Date of Patent: *Jan. 19, 2010

(54) METAL ALLOY FOR A STENT

(75) Inventors: Joseph G. Furst, Lyndhurst, OH (US);
Raymond W. Buckman, Jr., Pittsburgh, PA (US); Udayan Patel, San Jose, CA (US)

(73) Assignee: ICON International Systems, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/272,289

(22) Filed: Nov. 17, 2008

(65) Prior Publication Data

US 2009/0076589 A1    Mar. 19, 2009

Related U.S. Application Data

(63) Continuation of application No. 11/282,461, filed on Nov. 18, 2005, now Pat. No. 7,452,502.

(60) Provisional application No. 60/658,226, filed on Mar. 3, 2005, provisional application No. 60/694,881, filed on Jun. 29, 2005, provisional application No. 60/694,891, filed on Jun. 29, 2005.

(51) Int. Cl.
*C22C 27/00* (2006.01)
*A61F 2/06* (2006.01)

(52) U.S. Cl. .................... 148/423; 148/407; 420/429; 420/433; 623/23.7

(58) Field of Classification Search ............... 148/423; 420/429, 433
See application file for complete search history.

(56) References Cited

U.S. PATENT DOCUMENTS

| | | | |
|---|---|---|---|
| 3,964,482 | A | 6/1976 | Gerstel |
| 5,059,205 | A | 10/1991 | El-Nounou et al. |
| 5,091,205 | A | 2/1992 | Fan |
| 5,226,909 | A | 7/1993 | Evans et al. |
| 5,252,288 | A | 10/1993 | Yamamoto et al. |
| 5,263,349 | A | 11/1993 | Felix et al. |
| 5,344,402 | A | 9/1994 | Crocker |
| 5,344,426 | A | 9/1994 | Lau et al. |
| 5,372,661 | A | 12/1994 | Felix |
| 5,437,744 | A | 8/1995 | Carlen |

(Continued)

FOREIGN PATENT DOCUMENTS

CA    2172187    6/2001

(Continued)

OTHER PUBLICATIONS

W.D. Klopp, Technology status of molybdenum and tungsten alloys, Space Nuclear Power Systems, Orbit Book Company, Malabar, FL, (1984), Ch. 42, p. 359-369.*

(Continued)

*Primary Examiner*—George Wyszomierski
*Assistant Examiner*—Mark L Shevin
(74) *Attorney, Agent, or Firm*—Fay Sharpe LLP; Brian E. Turung

(57) ABSTRACT

A stent that is at least partially formed of a novel metal alloy, which novel metal alloy improves the physical properties of the stent.

33 Claims, 1 Drawing Sheet

U.S. PATENT DOCUMENTS

| | | | |
|---|---|---|---|
| 5,443,498 | A | 8/1995 | Fontaine |
| 5,605,696 | A | 2/1997 | Eury |
| 5,628,787 | A | 5/1997 | Mayer |
| 5,632,840 | A | 5/1997 | Campbell |
| 5,649,977 | A | 7/1997 | Campbell |
| 5,755,770 | A | 5/1998 | Ravenscroft |
| 5,800,511 | A | 9/1998 | Mayer |
| 5,824,046 | A | 10/1998 | Smith et al. |
| 5,824,077 | A | 10/1998 | Mayer |
| 5,843,172 | A | 12/1998 | Yan |
| 5,891,191 | A | 4/1999 | Stinson |
| 5,916,263 | A | 6/1999 | Goicoechea et al. |
| 5,919,570 | A | 7/1999 | Hostettler et al. |
| 5,951,585 | A | 9/1999 | Cathcart et al. |
| 5,957,930 | A | 9/1999 | Vrba |
| 5,993,545 | A | 11/1999 | Lupton |
| 6,039,920 | A | 3/2000 | Koch |
| 6,102,979 | A | 8/2000 | Bianco et al. |
| 6,123,712 | A | 9/2000 | DiCaprio et al. |
| 6,137,060 | A | 10/2000 | Avellanet |
| 6,238,491 | B1 | 5/2001 | Davidson et al. |
| 6,240,616 | B1 | 6/2001 | Yan |
| 6,253,443 | B1 | 7/2001 | Johnson |
| 6,273,908 | B1 | 8/2001 | Ndondo-Lay |
| 6,290,721 | B1 | 9/2001 | Heath |
| 6,379,380 | B1 | 4/2002 | Satz |
| 6,527,802 | B1 | 3/2003 | Mayer |
| 6,638,301 | B1 | 10/2003 | Chandrasekaran et al. |
| 6,702,849 | B1 | 3/2004 | Dutta et al. |
| 6,709,379 | B1 | 3/2004 | Brandau et al. |
| 6,723,120 | B2 | 4/2004 | Yan |
| 6,730,699 | B2 | 5/2004 | Li et al. |
| 6,749,554 | B1 | 6/2004 | Snow et al. |
| 6,764,505 | B1 | 7/2004 | Hossainy et al. |
| 6,790,218 | B2 | 9/2004 | Jayaraman |
| 6,790,372 | B2 | 9/2004 | Roy |
| 6,830,638 | B2 | 12/2004 | Boylan et al. |
| 6,865,810 | B2 | 3/2005 | Stinson |
| 6,920,677 | B2 | 7/2005 | Dolan et al. |
| 6,924,087 | B2 | 8/2005 | Yeshurun |
| 2001/0013166 | A1 | 8/2001 | Yan |
| 2002/0098278 | A1 | 7/2002 | Bates |
| 2002/0193865 | A1 | 12/2002 | Radisch |
| 2003/0040790 | A1 | 2/2003 | Furst |
| 2003/0077200 | A1 | 4/2003 | Craig |
| 2003/0100499 | A1 | 5/2003 | Epstein |
| 2003/0181972 | A1 | 9/2003 | Jansen |
| 2004/0000046 | A1 | 1/2004 | Stinson |
| 2004/0049261 | A1* | 3/2004 | Xu .................. 623/1.15 |
| 2004/0073291 | A1 | 4/2004 | Brown |
| 2004/0086674 | A1 | 5/2004 | Holman |
| 2004/0143317 | A1 | 7/2004 | Stinson |
| 2004/0230290 | A1 | 11/2004 | Weber |
| 2004/0243225 | A1 | 12/2004 | Ragheb |
| 2004/0265615 | A1 | 12/2004 | Kodas |
| 2005/0092507 | A1 | 5/2005 | Marshall |
| 2005/0131522 | A1 | 6/2005 | Stinson |
| 2005/0150096 | A1 | 7/2005 | Stinson |
| 2005/0182482 | A1 | 8/2005 | Wang |
| 2005/0216075 | A1 | 9/2005 | Wang |
| 2005/0238522 | A1 | 10/2005 | Leonhardt et al. |
| 2006/0136051 | A1 | 6/2006 | Furst et al. |
| 2007/0003753 | A1 | 1/2007 | Asgari |

FOREIGN PATENT DOCUMENTS

| | | |
|---|---|---|
| EP | 734721 | 2/1996 |
| EP | 714640 | 6/1996 |
| EP | 756853 | 2/1997 |
| SU | 333209 | 6/2006 |
| WO | WO 93/19803 | 10/1993 |
| WO | WO 95/30384 | 11/1995 |
| WO | WO 01/41678 | 6/2001 |

OTHER PUBLICATIONS

A.J. Mueller, et al, Evaluation of oxide dispersion strengthened (ODS) molybdenum and molybdenum-rhenium alloys, B-T-3148, (1999), p. 1-18.*

Metals handbook Desk Edition, $2^{nd}$ Edition. Copyright 1998 by ASM Intl.

Refractory Metals Forum: Rhenium and Its Alloys, B.D. Bryskin, Sep. 1992.

The Effect of Annealing Practice on the Structure and Mechanical Properties of P/M MO—47.5% Re Alloy, John A. Shields, Jr. Climax Specialty Metals, Cleveland, OH 44117.

Delute Mo-Re Alloys—A Critical Evaluation of Their Comparative Mechanical Properties, J. Watsworth, T.T. Nieg, and J.J. Stephens, Dec. 6, 1985.

Technology Status of Molybdenum and Tungsten Alloys, W.D. Klopp, Materials Consultant, 1542 Mendelssohn Dr., Westlake, OH 44145, 1985.

The Alloys of Rhenium with Molybdenum or with Tungsten and Having Good High Temperature Properties, G.A. Geach and J.E. Hughes, 1956.

Behaviour of Tungsten, Molybdenum, and Alloys under Unusual Heating Conditions, Ralf Eck, Hubert Bildstein, Fritz Simader, Roland Stickler, Josef Tinzl, 1989.

Rhenium and Molybdenum/Tungsten Based Alloys: An Overview of Database, Boris D. Bryskin and Jan C. Carlen 1998.

Mechanical Properties of Mo-Re Alloys at Different Test Temperatures, A.V. Abramyan, N.N. Morgunova, S.A. Golovanenko, and N.I. Kazakova, 1988.

Needles, Sutures and Knots, Part III; Specific Suture Materials Al Sherbeeny,M., MD, vol. 1, Jul. 2004.

Microsystems for Drug and Gene Delivery, Michael L. Reed, Senior Member, IEEE & WHYE-KEI LYE, Member, IEEE, 2004.

Silicon Micromachined Hollow Microneedles for Transdermal Liquid Transport, Jan J.G.E. Gardeniers, Regina Luttge, Erwin J.W. Berenschot, Meint J. De Boer, Shuki Y. Yeshurun, Meir Hefetz, Ronnyb van't Oever, and Abert van den Berg, Journal of Microelectromechanical Systems, vol. 12, No. 6, Dec. 2003.

A New Method for the Estimation for the Absorption Time of Bioabsorbable Polymers in the Body, D.C.tunc, M. Gockbora and P.Higham/ Stryker Howmedica Osteonics, Advanced Technology Group, Mahwa, NJ 07430 USA vol. 15, No. 6, Jun. 2002.

Synthesis and comparative biodegradability studies of three poly(alkylene succinate)s. D. Bikiaris, G. Papageorgiou, D. Achilias, Laboratory of Organic Chemical Technology, Dept. of Chemistry, Aristotle University of Thessaloniki, GR-541 24, Thessaloniki, Macedonia, Greece, 2006.

Leonhardt et al., "Investigation of Mechanical Properties and Microstructure of Various Molybdenum-Rhenium Alloys", AIP Conference Proceedings, vol. 458, p. 685, 1999.

Freund et al., "Stress-Rupture Strength and Creep Behaviour on Molybdenum-Rhenium Alloys", TMS $129^{th}$ Annual Meeting & Exhibtion, Mar. 12-16, 2000.

A.J. Mueller et al., Evaluation of oxide dispersion strengthened (ODS) molybdenum and molybdenum-rhenium alloys, B-T-3148M (1999), p. 1-18.

* cited by examiner

METAL ALLOY FOR A STENT

The present invention is a continuation of U.S. patent application Ser. No. 11/282,461 filed Nov. 18, 2005, now U.S. Pat. No. 7,452,502 which in turn claims priority on U.S. Provisional Application Ser. Nos. 60/658,226 filed Mar. 3, 2005 entitled "Improved Metal Alloys for Medical Devices"; 60/694,881 filed Jun. 29, 2005 entitled "Improved Metal Alloys for Medical Devices"; and 60/694,891 filed Jun. 29, 2005 entitled "Improved Metal Alloys for Medical Devices", all of which are incorporated herein by reference.

The invention relates generally to medical devices, and particularly to a medical device that is at least partially formed of a novel molybdenum and rhenium metal alloy, and more particularly to a stent that is at least partially formed of the novel metal alloy and which stent is useful in treating a body passageway.

BACKGROUND OF THE INVENTION

Medical treatment of various illnesses or diseases commonly includes the use of one or more medical devices. Two types of medical devices that are commonly used to repair various types of body passageways are an expandable graft or stent, or a surgical graft. These devices have been implanted in various areas of the mammalian anatomy. One purpose of a stent is to open a blocked or partially blocked body passageway. When a stent is used in a blood vessel, the stent is used to open the occluded vessel to achieve improved blood flow which is necessary to provide for the anatomical function of an organ. The procedure of opening a blocked or partially blocked body passageway commonly includes the use of one or more stents in combination with other medical devices such as, but not limited to, an introducer sheath, a guiding catheter, a guide wire, an angioplasty balloon, etc.

Various physical attributes of a stent can contribute directly to the success rate of the device. These physical attributes include radiopacity, hoop strength, radial force, thickness of the metal, dimensions of the metal and the like. Cobalt and chromium alloy and stainless steel are commonly used to form stents. These materials are commonly used since such materials having a known history of safety, effectiveness and biocompatibility. These materials however have limited physical performance characteristics as to size, strength, weight, bendability, biostability and radiopacity.

The present invention can be generally directed to a medical device such as, but not limited to, a stent that is at least partially formed of a novel metal alloy that improves the physical properties of the medical device thereby improving the success rate of such medical device.

SUMMARY OF THE INVENTION

The present invention is generally directed to a medical device that is at least partially made of a novel metal alloy having improved properties as compared to past medical devices. The novel metal alloy used to at least partially form the medical device improves one or more properties (e.g., strength, durability, hardness, biostability bendability, coefficient of friction, radial strength, flexibility, tensile strength, tensile elongation, longitudinal lengthening, stress-strain properties, improved recoil properties, radiopacity, heat sensitivity, biocompatibility, etc.) of such medical device. These one or more improved physical properties of the novel metal alloy can be achieved in the medical device without having to increase the bulk, volume and/or weight of the medical device, and in some instances these improved physical properties can be obtained even when the volume, bulk and/or weight of the medical device is reduced as compared to medical devices that are at least partially formed from traditional stainless steel or cobalt and chromium alloy materials. The novel metal alloy that is used to at least partially form the medical device can thus 1) increase the radiopacity of the medical device, 2) increase the radial strength of the medical device, 3) increase the yield strength and/or ultimate tensile strength of the medical device, 4) improve the stress-strain properties of the medical device, 5) improve the crimping and/or expansion properties of the medical device, 6) improve the bendability and/or flexibility of the medical device, 7) improve the strength and/or durability of the medical device, 8) increase the hardness of the medical device, 9) improve the longitudinal lengthening properties of the medical device, 10) improved the recoil properties of the medical device, 11) improve the friction coefficient of the medical device, 12) improve the heat sensitivity properties of the medical device, 13) improve the biostability and, or biocompatibility properties of the medical device, and/or 14) enable smaller, thinner and/or lighter weight medical devices to be made. The medical device generally includes one or more materials that impart the desired properties to the medical device so as to withstand the manufacturing processes that are needed to produce the medical device. These manufacturing processes can include, but are not limited to, laser cutting, etching, crimping, annealing, drawing, pilgering, electroplating, electro-polishing, chemical polishing, cleaning, pickling, ion beam deposition or implantation, sputter coating, vacuum deposition, etc.

In one non-limiting aspect of the present invention, a medical device that can include the novel metal alloy is a stent for use in a body passageway; however, it can be appreciated that other types of medical devices could be at least partially formed from the novel metal alloy. As used herein, the term "body passageway" is defined to be any passageway or cavity in a living organism (e.g., bile duct, bronchiole tubes, nasal cavity, blood vessels, heart, esophagus, trachea, stomach, fallopian tube, uterus, ureter, urethra, the intestines, lymphatic vessels, nasal passageways, eustachian tube, acoustic meatus, etc.). The techniques employed to deliver the medical device to a treatment area include, but are not limited to, angioplasty, vascular anastomoses, interventional procedures, and any combinations thereof. For vascular applications, the term "body passageway" primarily refers to blood vessels and chambers in the heart. The stent can be an expandable stent that is expandable by a balloon and/or other means. The stent can have many shapes and forms. Such shapes can include, but are not limited to, stents disclosed in U.S. Pat. Nos. 6,206,916 and 6,436,133; and all the prior art cited in these patents. These various designs and configurations of stents in such patents are incorporated herein by reference.

In another and/or alternative non-limiting aspect of the present invention, the stent is generally designed to include at least about 25 weight percent of the novel metal alloy; however, this is not required. In one non-limiting embodiment of the invention, the stent includes at least about 40 weight percent of the novel metal alloy. In another and/or alternative non-limiting embodiment of the invention, the stent includes at least about 50 weight percent of the novel metal alloy. In still another and/or alternative non-limiting embodiment of the invention, the stent includes at least about 60 weight percent of the novel metal alloy. In yet another and/or alternative non-limiting embodiment of the invention, the stent includes at least about 70 weight percent of the novel metal alloy. In still yet another and/or alternative non-limiting embodiment of the invention, the stent includes at least about 85 weight percent of the novel metal alloy. In a further and/or alternative non-limiting embodiment of the invention, the stent includes at least about 90 weight percent of the novel metal alloy. In still a further and/or alternative non-limiting embodiment of the invention, the stent includes at least about 95 weight percent of the novel metal alloy. In yet a further and/or alternative non-limiting embodiment of the invention, the stent includes about 100 weight percent of the novel metal alloy.

In still another and/or alternative non-limiting aspect of the present invention, the novel metal alloy that is used to form all or part of the stent 1) is not clad, metal sprayed, plated and/or formed (e.g., cold worked, hot worked, etc.) onto another metal, or 2) does not have another metal or metal alloy metal sprayed, plated, clad and/or formed onto the novel metal alloy. It will be appreciated that in some applications, the novel metal alloy of the present invention may be clad, metal sprayed, plated and/or formed onto another metal, or another metal or metal alloy may be plated, metal sprayed, clad and/or formed onto the novel metal alloy when forming all or a portion of a stent.

In yet another and/or alternative non-limiting aspect of the present invention, the novel metal alloy that is used to form all or a portion of the stent includes a majority weight percent rhenium and molybdenum. The novel alloy can include one or more other metals such as, but not limited to, calcium, chromium, cobalt, copper, gold, iron, lead, magnesium, nickel, niobium, platinum, rare earth metals, silver, tantalum, titanium, tungsten, yttrium, zinc, zirconium, and/or alloys thereof. In one non-limiting composition, the content of molybdenum and rhenium in the novel metal alloy is at least about 90 weight percent. In another and/or alternative non-limiting composition, the content of molybdenum and rhenium in the novel metal alloy is at least about 95 weight percent. In still another and/or alternative non-limiting composition, the content of molybdenum and rhenium in the novel metal alloy is at least about 98 weight percent. In yet another and/or alternative non-limiting composition, the content of molybdenum and rhenium in the novel metal alloy is at least about 99 weight percent. In still yet another and/or alternative non-limiting composition, the content of molybdenum and rhenium in the novel metal alloy is at least about 99.5 weight percent. In a further one non-limiting composition, the content of molybdenum and rhenium in the novel metal alloy is at least about 99.9 weight percent. In still a further and/or alternative non-limiting composition, the content of molybdenum and rhenium in the novel metal alloy is at least about 99.95 weight percent. In yet a further and/or alternative non-limiting composition, the content of molybdenum and rhenium in the novel metal alloy is at least about 99.99 weight percent. As can be appreciated, other weight percentages of the rhenium and molybdenum content of the novel metal alloy can be used. In one non-limiting composition, the purity level of the novel metal alloy is such so as to produce a solid solution of the novel metal alloy. A solid solution or homogeneous solution is defined as a metal alloy that includes two or more primary metals and the combined weight percent of the primary metals is at least about 95 weight percent, typically at least about 99 weight percent, more typically at least about 99.5 weight percent, even more typically at least about 99.8 weight percent, and still even more typically at least about 99.9 weight percent. A primary metal is a metal component of the metal alloy that is not a metal impurity. A solid solution of a novel metal alloy that includes rhenium and molybdenum as the primary metals is an alloy that includes at least about 95-99 weight percent rhenium and molybdenum. It is believed that a purity level of less than 95 weight percent molybdenum and rhenium adversely affects one or more physical properties of the metal alloy that are useful or desired in forming and/or using a stent. In one embodiment of the invention, the rhenium content of the novel metal alloy in accordance with the present invention is at least about 40 weight percent. In one non-limiting composition, the rhenium content of the novel metal alloy is at least about 45 weight percent. In still another and/or alternative non-limiting composition, the rhenium content of the novel metal alloy is about 45-50 weight percent. In yet another and/or alternative non-limiting composition, the rhenium content of the novel metal alloy is about 47-48 weight percent. In still yet another and/or alternative non-limiting composition, the rhenium content of the novel metal alloy is about 47.6-49.5 weight percent. As can be appreciated, other weight percentages of the rhenium content of the novel metal alloy can be used. In another and/or alternative embodiment of the invention, the molybdenum content of the novel metal alloy in accordance with the present invention is at least about 40 weight percent. In one non-limiting composition, the molybdenum content of the novel metal alloy is at least about 45 weight percent. In another and/or alternative non-limiting composition, the molybdenum content of the novel metal alloy is at least about 50 weight percent. In still another and/or alternative non-limiting composition, the molybdenum content of the novel metal alloy is about 50-60 percent. In yet another and/or alternative non-limiting composition, the molybdenum content of the novel metal alloy is about 50-56 weight percent. As can be appreciated, other weight percentages of the molybdenum content of the novel metal alloy can be used.

In still another and/or alternative non-limiting aspect of the present invention, the novel metal alloy includes less than about 5 weight percent other metals and/or impurities. A high purity level of the novel metal alloy results in the formation of a more homogeneous alloy which in turn results in a more uniform density throughout the novel metal alloy, and also results in the desired yield and ultimate tensile strengths of the novel metal alloy. The density of the novel metal alloy is generally at least about 12 gm/cc, and typically at least about 13 gm/cc. This substantially uniform high density of the novel metal alloy significantly improves the radiopacity of the novel metal alloy. In one non-limiting composition, the novel metal alloy includes less than about 1 weight percent other metals and or impurities. In another and/or alternative non-limiting composition, the novel metal alloy includes less than about 0.5 weight percent other metals and/or impurities. In still another and/or alternative non-limiting composition, the novel metal alloy includes less than about 0.4 weight percent other metals and/or impurities. In yet another and/or alternative non-limiting composition, the novel metal alloy includes less than about 0.2 weight percent other metals and/or impurities. In still yet another and/or alternative non-limiting composition, the novel metal alloy includes less than about 0.1 weight percent other metals and/or impurities. In a further and/or alternative non-limiting composition, the novel metal alloy includes less than about 0.05 weight percent other metals and/or impurities. In still a further and/or alternative non-limiting composition, the novel metal alloy includes less than about 0.02 weight percent other metals and/or impurities. In yet a further and/or alternative non-limiting composition, the novel metal alloy includes less than about 0.01 weight percent other metals and/or impurities. As can be appreciated, other weight percentages of the amount of other metals and/or impurities in the novel metal alloy can exist.

In yet another and/or alternative non-limiting aspect of the present invention, the novel metal alloy includes a certain amount of carbon and oxygen. These two elements have been found to affect the forming properties and brittleness of the novel metal alloy. The controlled atomic ratio of carbon and oxygen in the novel metal alloy also can be used to minimize the tendency of the novel metal alloy to form micro-cracks during the forming of the novel alloy into a stent, and/or during the expansion of the stent in a body passageway. In one non-limiting embodiment of the invention, the novel metal alloy includes up to about 200 ppm carbon and up to about 150 ppm oxygen. Higher carbon and oxygen contents in the novel metal alloy is believed to adversely affect one or more physical properties of the metal alloy that are useful or desired in forming and/or using a stent. In one non-limiting formulation, the novel metal alloy includes up to about 150 ppm carbon. In still another and/or alternative non-limiting formulation, the novel metal alloy includes up to about 100 ppm carbon. In yet another and/or alternative non-limiting formulation, the novel metal alloy includes less than about 50 ppm carbon. In still yet another and/or alternative non-limiting formulation, the novel metal alloy includes up to about 100 ppm oxygen. In a further and/or alternative non-limiting formulation, the novel metal alloy includes up to about 75 ppm oxygen. In still a further and/or alternative non-limiting formulation, the novel metal alloy includes up to about 50 ppm oxygen. In yet a further and/or alternative non-limiting formulation, the novel metal alloy includes up to about 30 ppm oxygen. In still yet a further and/or alternative non-limiting formulation, the novel metal alloy includes less than about 20 ppm oxygen. In yet a further and/or alternative non-limiting formulation, the novel metal alloy includes less than about 10 ppm oxygen. As can be appreciated, other amounts of carbon and/or oxygen in the novel metal alloy can exist. In another and/or alternative non-limiting embodiment of the invention, the carbon to oxygen atomic ratio in the novel metal alloy is generally at least about 2:1 (i.e., weight ratio of about 1.5:1). The control of the atomic ratio of carbon to oxygen in the novel metal alloy allows for the redistribution of oxygen in the metal alloy so as to minimize the tendency of micro-cracking in the novel metal alloy during the forming of the novel alloy into a medical device, and/or during the use and/or expansion of the medical device in a body passageway. When the carbon to oxygen atomic ratio falls below 2-2.5:1 (i.e., weight ratio of about 1.5-1.88:1), the degree of elongation of the novel metal alloy decreases and the incidence of micro-cracking increases, thus adversely affecting one or more physical properties of the metal alloy that are useful or desired in forming and/or using the stent. In one non-limiting formulation, the carbon to oxygen atomic ratio in the novel metal alloy is generally at least about 2.5:1 (i.e., weight ratio of about 1.88:1). In another and/or alternative non-limiting formulation, the carbon to oxygen atomic ratio in the novel metal alloy is generally at least about 3:1 (i.e., weight ratio of about 2.25:1). In still another and/or alternative non-limiting formulation, the carbon to oxygen atomic ratio in the novel metal alloy is generally at least about 4:1 (i.e., weight ratio of about 3:1). In yet another and/or alternative non-limiting formulation, the carbon to oxygen atomic ratio in the novel metal alloy is generally at least about 5:1 (i.e., weight ratio of about 3.75:1). In still yet another and/or alternative non-limiting formulation, the carbon to oxygen atomic ratio in the novel metal alloy is generally about 2.5-50:1 (i.e. weight ratio of about 1.88-37.54:1). In a further and/or alternative non-limiting formulation, the carbon to oxygen atomic ratio in the novel metal alloy is generally about 2.5-20:1 (i.e., weight ratio of about 1.88-15:1). In still a further and/or alternative non-limiting formulation, the carbon to oxygen atomic ratio in the novel metal alloy is generally about 2.5-10:1 (i.e. weight ratio of about 1.88-7.5:1). In yet a further and/or alternative non-limiting formulation, the carbon to oxygen atomic ratio in the novel metal alloy is generally about 2.5-5:1 (i.e., weight ratio of about 1.88-3.75:1). As can be appreciated, other atomic ratios of the carbon to oxygen in the novel metal alloy can be used.

In still yet another and/or alternative non-limiting aspect of the present invention, the novel metal alloy includes a controlled amount of nitrogen. Large amounts of nitrogen in the novel metal alloy can adversely affect the ductility of the novel metal alloy. This can in turn adversely affect the elongation properties of the novel metal alloy. A nitrogen content in the novel metal alloy of over 20 ppm can begin to cause the ductility of the novel metal alloy to unacceptably decrease, thus adversely affect one or more physical properties of the metal alloy that are useful or desired in forming and/or using the stent. In one non-limiting embodiment of the invention, the novel metal alloy includes less than about 30 ppm nitrogen. In one non-limiting formulation, the novel metal alloy includes less than about 25 ppm nitrogen. In still another and/or alternative non-limiting formulation, the novel metal alloy includes less than about 10 ppm nitrogen. In yet another and/or alternative non-limiting formulation, the novel metal alloy includes less than about 5 ppm nitrogen. As can be appreciated, other amounts of nitrogen in the novel metal alloy can exist.

In a further and/or alternative non-limiting aspect of the present invention, the novel metal alloy has several physical properties that positively affect the stent when at least partially formed of the novel metal alloy. In one non-limiting embodiment of the invention, the average hardness of the novel metal alloy tube used to form the stent is generally at least about 60 (HRC) at 77° F. In one non-limiting aspect of this embodiment, the average hardness of the novel metal alloy tube used to form the stent is generally at least about 70 (HRC) at 77° F. and typically about 80-100 (HRC) at 77° F. In another and/or alternative non-limiting embodiment of the invention, the average ultimate tensile strength of the novel metal alloy used to form the stent is generally at least about 60 UTS (ksi). In non-limiting aspect of this embodiment, the average ultimate tensile strength of the novel metal alloy used to form the stent is generally at least about 70 UTS (ksi), typically about 80-150 UTS (ksi), and more typically about 100-150 UTS (ksi). In still another and or alternative non-limiting embodiment of the invention, the average yield strength of the novel metal alloy used to form the stent is at least about 70 ksi. In one non-limiting aspect of this embodiment, the average yield strength of the novel metal alloy used to form the stent is at least about 80 ksi, and typically about 98-122 (ksi). In yet another and/or alternative non-limiting embodiment of the invention, the average grain size of the novel metal alloy used to form the stent is greater than 5 ASTM (e.g., ASTM E 112-96). The small grain size of the novel metal alloy enables the stent to have the desired elongation and ductility properties that are useful in enabling the stent to be formed, crimped and/or expanded. In one non-limiting aspect of this embodiment, the average grain size of the novel metal alloy used to form the stent is about 5.2-10 ASTM, typically about 5.5-9 ASTM, more typically about 6-9 ASTM, still more typically about 6-8 ASTM, even more typically about 6-7 ASTM, and still even more typically about 6.5-7 ASTM. In still yet another and/or alternative non-limiting embodiment of the invention, the average tensile elongation of the novel metal alloy used to form the stent is at least about 25%. An average tensile elongation of at least 25% for the novel metal alloy is important to enable the stent to be properly expanded when positioned in the treatment area of a body passageway. A stent that does not have an average tensile elongation of at least about 25% can form microcracks and/or break during the forming, crimping and/or expansion of the stent. In one non-limiting aspect of this embodiment, the average tensile elongation of the novel metal alloy used to form the stent is about 25-35%. In another and/or alternative non-limiting aspect of this embodiment, the average tensile elongation of the novel metal alloy used to form the stent is about 28-32%. The unique combination of the rhenium content in the metal alloy in combination with achieving the desired purity and composition of the alloy and the desired grain size of the metal alloy results in 1) a stent having the desired high ductility at about room temperature, 2) a stent having the desired amount of tensile elongation, 3) a homogeneous or solid solution of a metal alloy having high radiopacity, 4) a reduction or prevention of microcrack formation and/or breaking of the metal alloy tube when the metal alloy tube is sized and/or cut to form the stent, 5) a reduction or prevention of microcrack formation and/or breaking of the stent when the stent is crimped onto a balloon and/or other type of medical device for insertion into a body passageway, 6) a reduction or prevention of microcrack formation and/or breaking of the stent when the stent is bent and or expanded in a body passageway, 7) a stent having the desired ultimate tensile strength and yield strength, 8) a stent that can have very thin wall thicknesses and still have the desired radial forces needed to retain the body passageway on an open state when the stent has been expanded, and/or 9) a stent that exhibits less recoil when the stent is crimped onto a delivery system and or expanded in a body passageway. Several non-limiting examples of the novel metal alloy in accordance with the present invention are set forth below:

| Metal/Wt. % | Ex. 1 | Ex. 2 | Ex. 3 |
|---|---|---|---|
| C | ≦150 ppm | ≦150 ppm | ≦150 ppm |
| Ca | 0% | 0% | 0% |
| Mg | 0% | 0% | 0% |
| Mo | 50-60% | 50-60% | 50-55% |
| O | ≦100 ppm | ≦100 ppm | ≦100 ppm |
| N | ≦40 ppm | ≦40 ppm | ≦40 ppm |
| Nb | 0% | ≦5% | 0% |
| Rare Earth Metal | 0% | ≦4% | 0% |
| Re | 40-50% | 40-50% | 45-50% |
| Ta | 0% | ≦3% | 0% |
| Ti | 0% | ≦1% | 0% |
| W | 0% | ≦3% | 0% |
| Y | 0% | ≦0.1% | 0% |
| Zn | 0% | ≦0.1% | 0% |
| Zr | 0% | ≦2% | 0% |

| Metal/Wt. % | Ex. 4 | Ex. 5 | Ex. 6 |
|---|---|---|---|
| C | ≦150 ppm | ≦150 ppm | ≦150 ppm |
| Ca | 0% | 0% | 0% |
| Mg | 0% | 0% | 0% |
| Mo | 52-55.5% | 51-58% | 50-56% |
| O | ≦100 ppm | ≦100 ppm | ≦100 ppm |
| N | ≦20 ppm | ≦20 ppm | ≦20 ppm |
| Rare Earth Metal | 0% | 0% | 0% |
| Re | 44.5-48% | 42-49% | 44-50% |
| Ta | 0% | 0% | 0% |
| Ti | 0% | 0% | 0% |
| W | 0% | 0% | 0% |
| Y | 0% | 0% | 0% |
| Zn | 0% | 0% | 0% |
| Zr | 0% | 0% | 0% |

In examples 1, 3-6 above, the novel metal alloy is principally formed of rhenium and molybdenum and the content of other metals and/or impurities is less than about 0.2 weight percent of the novel metal alloy. In examples 1-6, the atomic ratio of carbon to oxygen is at least about 2.5:1 (i.e., weight ratio of carbon to oxygen of at least about 1.88:1) and the average grain size is about 6-10 ASTM.

Three additional non-limiting examples of the novel metal alloy in accordance with the present invention are set forth below:

| Metal/Wt. % | Ex. 7 | Ex. 8 | Ex. 9 |
|---|---|---|---|
| C | <150 ppm | <50 ppm | <50 ppm |
| Mo | 51-54% | 52.5-55.5% | 50.5-52.4% |
| O | <50 ppm | <10 ppm | <10 ppm |
| N | <20 ppm | <10 ppm | <10 ppm |
| Re | 46-49% | 44.5-47.5% | 47.6-49.5% |

In examples 7-9 above, the novel metal alloy is principally formed of rhenium and molybdenum and the content of other metals and/or impurities is less than about 0.1 weight percent of the novel metal alloy, the atomic ratio of carbon to oxygen is about 2.5-10:1 (i.e., weight ratio of about 1.88-7.5:1), the average grain size of the novel metal alloy is about 6-9 ASTM, the tensile elongation of the metal alloy is about 25-35%, the average density of the metal alloy is at least about 13.4 gm/cc, the average yield strength of the metal alloy is about 98-122 (ksi), the average ultimate tensile strength of the metal alloy is about 100-150 UTS (ksi), and the average hardness of the metal alloy is about 80-100 (HRC) at 77° F.

In another and/or alternative non-limiting aspect of the present invention, the use of the novel metal alloy in the stent can increase the strength of the stent as compared with stainless steel or chromium-cobalt alloys, thus less quantity of novel metal alloy can be used in the stent to achieve similar strengths as compared to stents formed of different metals. As such, the resulting stent can be made smaller and less bulky by use of the novel metal alloy without sacrificing the strength and durability of the stent. Such a stent can have a smaller profile, thus can be inserted in smaller areas, openings and/or passageways. The novel metal alloy also can increase the radial strength of the stent. For instance, the thickness of the walls of the stent and/or the wires used to form the stent can be made thinner and achieve a similar or improved radial strength as compared with thicker walled stents formed of stainless steel or cobalt and chromium alloy. The novel metal alloy also can improve stress-strain properties, bendability and flexibility of the stent, thus increase the life of the stent. For instance, the stent can be used in regions that subject the stent to bending. Due to the improved physical properties of the stent from the novel metal alloy, the stent has improved resistance to fracturing in such frequent bending environments. In addition or alternatively, the improved bendability and flexibility of the stent due to the use of the novel metal alloy can enable the stent to be more easily inserted into a body passageway. The novel metal alloy can also reduce the degree of recoil during the crimping and/or expansion of the stent. For example, the stent better maintains its crimped form and/or better maintains its expanded form after expansion due to the use of the novel metal alloy. As such, when the stent is to be mounted onto a delivery device when the stent is crimped, the stent better maintains its smaller profile during the insertion of the stent in a body passageway. Also, the stent better maintains its expanded profile after expansion so as to facilitate in the success of the stent in the treatment area. In addition to the improved physical properties of the stent by use of the novel metal alloy, the novel metal alloy has improved radiopaque properties as compared to standard materials such as stainless steel or cobalt-chromium alloy, thus reducing or eliminating the need for using marker materials on the stent. For instance, the novel metal alloy is at least about 10-20% more radiopaque than stainless steel or cobalt-chromium alloy. Specifically, the novel metal alloy can be at least about 33% more radiopaque than cobalt-chromium alloy and at least about 41.5% more radiopaque than stainless steel.

In still yet another and/or alternative non-limiting aspect of the present invention, the stent that is at least partially formed from the novel metal alloy can be formed by a variety of manufacturing techniques. In one non-limiting embodiment of the invention, the stent can be formed from a rod or tube of the novel metal alloy. If a solid rod of the novel metal alloy is formed, the rod can be drilled (e.g., gun drilled, EDM, etc.) to form a cavity or passageway partially or fully through the rod. The rod or tube can be cleaned, polished, annealed, drawn, etc. to obtain the desired diameter and/or wall thickness of the metal tube. After the metal tube has been formed to the desired diameter and wall thickness, the metal tube can be formed into a stent by a process such as, but not limited to laser cutting, etching, etc. After the stent has been formed, the stent can be cleaned, polished, sterilized, etc. for final processing of the stent.

In another and/or alternative non-limiting aspect of the invention, the stent can include a bistable construction. In such a design, the stent has two or more stable configurations, including a first stable configuration with a first cross-sectional shape and a second stable configuration with a second cross-sectional shape. All or a portion of the stent can include the bistable construction. The bistable construction can result in a generally uniform change in shape of the stent, or one portion of the stent can change into one or more configurations and one or more other portions of the stent can change into one or more other configurations.

In still another and/or alternative aspect of the invention, the stent can be an expandable device that can be expanded by use of a some other device (e.g., balloon, etc.) and/or is self expanding. The expandable stent can be at least partially fabricated from a material that has no or substantially no shape memory characteristics and/or can be at least partially fabricated from a material having shape-memory characteristics.

In one non-limiting application of the present invention, there is provided a medical device in the form of a stent that is at least partially formed of a novel metal alloy. The novel metal alloy imparts one or more improved physical characteristics to the stent (e.g., strength, durability, hardness, biostability, bendability, coefficient of friction, radial strength, flexibility, tensile strength, elongation, longitudinal lengthening, stress-strain properties, improved recoil properties, radiopacity, heat sensitivity, biocompatibility, etc.). The novel metal alloy includes at least about 99 weight percent rhenium and molybdenum. The stent can have a variety of applications such as, but not limited to placement into the vascular system, esophagus, trachea, colon, biliary tract, or urinary tract; however, the stent can have other applications. The stent can have one or more body members, wherein each body member includes first and second ends and a wall surface disposed between the first and second ends. Each body member can have a first cross-sectional area which permits delivery of the body member into a body passageway, and a second, expanded cross-sectional area. The expansion of the stent body member can be accomplished in a variety of manners. Typically, the body member is expanded to its second cross-sectional area by a radially, outwardly extending force applied at least partially from the interior region of the body member (e.g., by use of a balloon, etc.); however, this is not required. When the second cross-sectional area is variable, the second cross-sectional area is typically dependent upon the amount of radially outward force applied to the body member. The stent can be designed such that the body member expands while retaining the original length of the body member; however, this is not required. The body member can have a first cross-sectional shape that is generally circular so as to form a substantially tubular body member; however, the body member can have other cross-sectional shapes. When the stent includes two of more body members, the two of more body members can be connected together by at least one connector member. The stent can include rounded, smooth and/or blunt surfaces to minimize and/or prevent damage to a body passageway as the stent is inserted into a body passageway and/or expanded in a body passageway; however, this is not required. The stent can be treated with gamma, beta and/or e-beam radiation, and/or otherwise sterilized; however, this is not required. The stent can have multiple sections. The sections of the stent can have a uniform architectural configuration, or can have differing architectural configurations. Each of the sections of the stent can be formed of a single part or formed of multiple parts which have been attached. When a section is formed of multiple parts, typically the section is formed into one continuous piece; however, this is not required. One or more portions of the stent can be coated with one or more biological agents. The one or more biological agents, when used, can be coated so as to be controllably or uncontrollably released from the stent.

The use of the novel metal alloy to form all or a portion of a stent results in several advantages over stent formed from other materials. These advantages include, but are not limited to, The novel metal alloy has increased strength as compared with stainless steel or chromium-cobalt alloys, thus less quantity of novel metal alloy can be used in the stent to achieve similar strengths as compared to stents formed of different metals. As such, the resulting stent can be made smaller and less bulky by use of the novel metal alloy without sacrificing the strength and durability of the stent. The stent can also have a smaller profile, thus can be inserted into smaller areas, openings and/or passageways. The increased strength of the novel metal alloy also results in the increased radial strength of the stent. For instance, the thickness of the walls of the stent and/or the wires used to form the stent can be made thinner and achieve a similar or improved radial strength as compared with thicker walled stents formed of stainless steel or cobalt and chromium alloy.

The novel metal alloy has improved stress-strain properties, bendability properties, elongation properties and/or flexibility properties of the stent as compared with stainless steel or chromium-cobalt alloys, thus resulting in an increase life for the stent. For instance, the stent can be used in regions that subject the stent to repeated bending. Due to the improved physical properties of the stent from the novel metal alloy, the stent has improved resistance to fracturing in such frequent bending environments. These improved physical properties at least in part result from the composition of the novel metal alloy; the grain size of the novel metal alloy; the carbon, oxygen and nitrogen content of the novel metal alloy; and/or the carbon/oxygen ratio of the novel metal alloy.

The novel metal alloy has a reduce the degree of recoil during the crimping and/or expansion of the stent as compared with stainless steel or chromium-cobalt alloys. The stent formed of the novel metal alloy better maintains its crimped form and/or better maintains its expanded form after expansion due to the use of the novel metal alloy. As such, when the stent is to be mounted onto a delivery device when the stent is crimped, the stent better maintains its smaller profile during the insertion of the stent in a body passageway. Also, the stent better maintains its expanded profile after expansion so as to facilitate in the success of the stent in the treatment area.

The novel metal alloy has improved radiopaque properties as compared to standard materials such as stainless steel or cobalt-chromium alloy, thus reducing or eliminating the need for using marker materials on the stent. For instance, the novel metal alloy is at least about 10-20% more radiopaque than stainless steel or cobalt-chromium alloy.

The novel metal alloy is less of an irritant to the body than stainless steel or cobalt-chromium alloy, thus can result in reduced inflammation, faster healing, increased success rates of the stent. When the stent is expanded in a body passageway, some minor damage to the interior of the passageway can occur. When the body begins to heal such minor damage, the body has less adverse reaction to the presence of the novel metal alloy than compared to other metals such as stainless steel or cobalt-chromium alloy.

One non-limiting object of the present invention is the provision of a medical device that is at least partially formed of a novel metal alloy.

Another and/or alternative non-limiting object of the present invention is the provision of a medical device having improved procedural success rates.

Still another and/or alternative non-limiting object of the present invention is the provision of a medical device that is formed of a material that improves the physical properties of the medical device.

Yet another and/or alternative non-limiting object of the present invention is the provision of a medical device that is at least partially formed of a novel metal alloy that has increased strength and can also be used as a marker material.

Still yet another and/or alternative non-limiting object of the present invention is the provision of a medical device that at least partially includes a novel metal alloy that enables the medical device to be formed with less material without sacrificing the strength of the medical device as compared to prior medical devices.

These and other advantages will become apparent to those skilled in the art upon the reading and following of this description taken together with the accompanying drawings.

BRIEF DESCRIPTION OF THE DRAWINGS

Reference may now be made to the drawings, which illustrate various embodiments that the invention may take in physical form and in certain parts and arrangements of parts wherein.

DETAILED DESCRIPTION OF THE INVENTION

Figure 1:
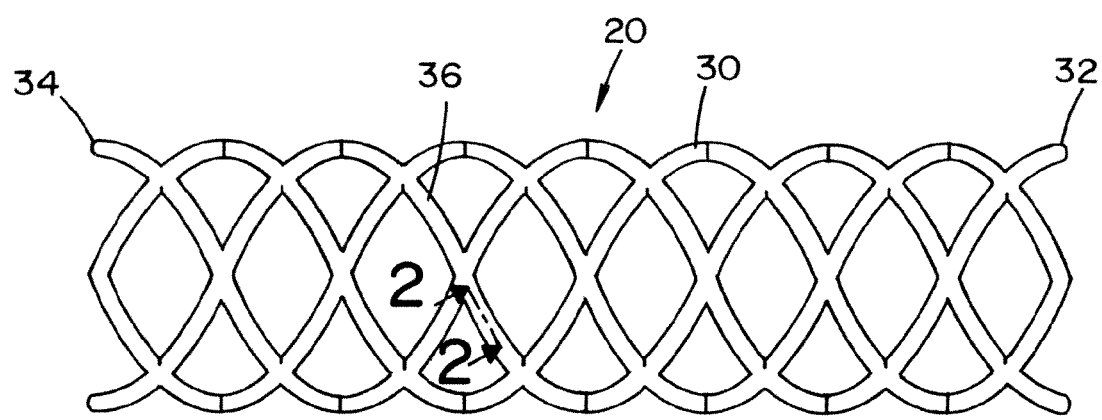
FIG. 1 is a perspective view of a section of a medical device in the form of an unexpanded stent which permits delivery of the stent into a body passageway; and, FIG. 2 is a cross-sectional view along line 2-2 of FIG. 1 illustrating the novel metal alloy material that forms the medical device.
Figure 2:
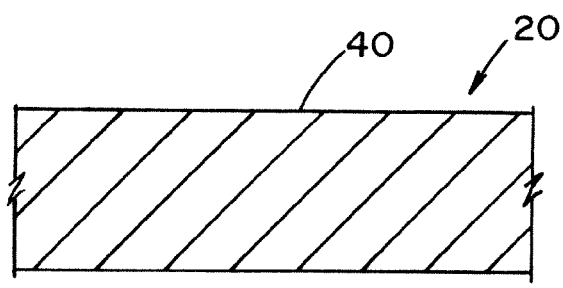

Referring now to the drawings wherein the showings are for the purpose of illustrating embodiments of the invention only and not for the purpose of limiting the same, FIGS. 1-2 disclose a medical device in the form of a stent for use in a body passageway. The stent of the present invention can be at least partially formed of a novel metal alloy having improved physical properties. The novel metal alloy used to at least partially form the stent improves one or more properties (e.g., strength, durability, hardness, biostability, bendability, coefficient of friction, radial strength, flexibility, tensile strength, tensile elongation, longitudinal lengthening, stress-strain properties, improved recoil properties, radiopacity, heat sensitivity, biocompatibility, etc.) of such stent. In some instances, the use of the novel metal alloy can reduce the volume, bulk and/or weight of the stent as compared to prior stents made from traditional materials; however, this is not required. The one or more materials used to form the stent include one or more properties which promote the success of the stent.

The stent illustrated in FIGS. 1-2 is designed to be insertable to a diseased area in a body passageway and to expand the diseased area to enable better or proper fluid flow through the body passageway; however, the stent can be used for other or additional reasons. In one specific non-limiting example, the stent can be used to open an obstructed blood vessel. Although FIGS. 1-2 illustrate the stent for use in the cardiovascular field, the stent can be used in other medical fields (e.g., orthopedic field, cardiology field, pulmonology field, urology field, nephrology field, gastrointerology field, gynecology field, otolaryngology field, etc.). The stent, when used in the cardiovascular field, can be used to address various medical problems such as, but not limited to, restenosis, atherosclerosis, atherogenesis, angina, ischemic disease, congestive heart failure or pulmonary edema associated with acute myocardial infarction, atherosclerosis, thrombosis, controlling blood pressure in hypertension, platelet adhesion, platelet aggregation, smooth muscle cell proliferation, vascular complications, wounds, myocardial infarction, pulmonary thromboembolism, cerebral thromboembolism, thrombophiebitis, thrombocytopenia and/or bleeding disorders.

The novel metal alloy that at least partially forms the stent includes a majority weight percent of Mo and Re. The novel metal alloy typically forms at least a majority weight percent of the stent; however, this is not required. As illustrated in FIGS. 1 and 2, the member structures 36 of stent 20 are formed of 98-100% of the novel metal alloy 40. In one non-limiting novel metal alloy composition, the metal alloy includes about 44-48 weight percent Re and about 52-56 weight percent Mo. In one non-limiting example, the novel metal alloy is a solid solution that includes about 44.5-47.5 weight percent Re and 52.5-55.5 weight percent Mo, a weight percent of Re plus Mo of at least about 99.9%, less than about 50 ppm carbon, less than about 10 ppm oxygen, less than about 20 ppm nitrogen, a carbon to oxygen atomic ratio of about 2.5-10:1, and no more than about 0.1 weight impurities. The tensile elongation of the novel metal alloy is about 25-35%, the average density of the novel metal alloy is at least about 13.4 gm/cc., the average yield strength of the novel metal alloy is about 98-122 (ksi), the average ultimate tensile strength of the novel metal alloy is about 100-150 UTS (ksi), and the average hardness of the novel metal alloy is about 80-100 (HRC) at 77° F. The 99.9 weight percent purity of the novel metal alloy forms a solid or homogenous solution. The unique combination of carbon and oxygen redistributes the oxygen at the grain boundary of the novel metal alloy, which in turn helps in reducing microcracks (defects) in the ultimately formed stent. The control of carbon to oxygen atomic ratio can also be used to obtain high ductility of the novel metal alloy, which can be measured in part as tensile elongation. This increase in tensile elongation is an important attribute when forming the novel metal alloy into the stent. The purity of the novel metal alloy also results in a substantially uniform density throughout the novel metal alloy. The density of the solid homogeneous solution of the novel metal alloy results in the high radiopacity of the novel metal alloy. The addition of rhenium in the novel metal alloy improves the ductility of the molybdenum. The solid or homogeneous solution of the novel metal alloy results in a novel metal alloy having the desired tensile yield strength and ultimate tensile strength of the novel metal alloy. Nitrogen in the novel metal alloy is an interstitial element that raises the Ductile Brittle Transition Temperature (DBTT). When the DBTT is too high, the novel metal alloy can become brittle. The maintenance of nitrogen below about 20 ppm overcomes this brittleness problem. The combination of these various properties of the solid or homogeneous solution of the novel metal alloy enables the novel metal alloy to be formed into a stent that has superior performance characteristics such as, but not limited tom high radiopacity with thinner and narrower struts and simultaneously having a radial force adequate to retain the vessel lumen fairly open and prevent any recoil. The novel metal alloy can be fabricated from a tubing with a outer diameter as small as about 0.070 inch and with a wall thickness as small as about 0.002 inch. In one particular design, the average wall thickness after the final processing of the alloy tube is about 0.0021-0.00362 inch, and the average concentricity deviation after the final processing of the alloy tube is about 1-20%. As can be appreciated, the size values of the processed alloy rod set forth above are merely exemplary for using the novel metal alloy to form a stent for use in the vascular system of a patient. When the novel metal alloy is used to form other types of stents for use in different regions of a body, the size values of the final processed novel metal alloy can be different. The solid or homogeneous solution of the novel metal alloy has the unique characteristics of purity, ductility, grain size, tensile elongation, yield strength, and tensile strength that permits the novel metal alloy to be fabricated into the stent tubing without creating microcracks that are detrimental to the stent properties.

Referring again to FIGS. 1-2, the stent is an expandable stent that can be used to at least partially expanding occluded segments of a body passageway; however, the stent can have other or additional uses. For example, the expandable stent can be used as, but not limited to, 1) a supportive stent placement within a blocked vasculature opened by transluminal recanalization, which are likely to collapse in the absence of an internal support; 2) forming a catheter passage through mediastinal and/or other veins occluded by inoperable cancers; 3) reinforcing a catheter creating intrahepatic communication between portal and/or hepatic veins in patients suffering from portal hypertension; 4) a supportive stent placement of narrowing of the esophagus, the intestine, the ureter and/or the urethra; and/or 5) a supportive stent reinforcement of reopened and previously obstructed bile ducts. Accordingly, use of the term "stent" encompasses the foregoing or other usages within various types of body passageways, and also encompasses use for expanding a body passageway. The stent can be implanted or applied in a body passageway by techniques such as, but not limited to, balloon delivery, sheath catheter delivery, etc.

As shown in FIG. 1, the stent 20 includes at least one body member 30 having a first end 32, a second end 34, and member structures 36 disposed between the first and second ends. The body member is typically tubular shaped; however, it can be appreciated that the stent can have a variety of shapes and/or configurations. As can also be appreciated, the stent can be formed of one body member of a plurality of body members that are connected together. Body member 30 has a first diameter which permits delivery of the body member into a body passageway. The first diameter of the body member is illustrated as substantially constant along the longitudinal length of the body member. As can be appreciated, the body member can have a varying first diameter along at least a portion of the longitudinal length of the body member. The body member also has a second expanded diameter, not shown. The second diameter typically varies in size; however, the second diameter can be non-variable. The stent can be expanded in a variety of ways such as by a balloon or be self expanding. A balloon expandable stent is typically premounted or crimped onto an angioplasty balloon catheter. The balloon catheter is then positioned into the patient via a guide wire. Once the stent is properly positioned, the balloon catheter is inflated to the appropriate pressure for stent expansion. After the stent has been expanded, the balloon catheter is deflated and withdrawn, leaving the stent deployed at the treatment site. The novel metal alloy that is used to at least partially form the stent has very little recoil, thus once the stent is expanded, the stent substantially retains its expanded shape.

One or more surfaces of the stent can be treated so as to have generally smooth surfaces. Generally, the ends are treated by filing, buffing, polishing, grinding, coating, and or the like; however, this is not required. As a result, sharp edges, pointed surfaces and the like are substantially eliminated from the end section of the stent. Typically most, if not all, the ends of the stent are treated to have smooth surfaces. The smooth surfaces of the ends reduce damage to surrounding tissue as the stent is positioned in and/or expanded in a body passageway. One or more portions of the stent can include one or more biological agents.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

We claim:

1. A medical device at least partially formed of a metal alloy which improves the strength and radiopacity of the medical device, said metal alloy including at least about 95 weight percent of a solid solution of rhenium and molybdenum, said metal alloy including 40-55 weight percent rhenium and 45-60 weight percent molybdenum, said metal alloy including carbon, nitrogen and oxygen, said metal alloy having a nitrogen content of less than about 20 ppm, a carbon content of less than about 150 ppm, and an oxygen content of less than about 75 ppm, said metal alloy having a carbon to oxygen atomic ratio of at least about 1:1, said metal alloy having a carbon to oxygen atomic ratio of less than about 50:1.

2. The medical device as defined in claim 1, wherein said metal alloy has an average yield strength of at least about 95 ksi and an average ultimate tensile strength of at least about 95 ksi, said metal alloy having an average grain size of over 5 ASTM, and said metal alloy having an average tensile elongation of at least about 25%.

3. The medical device as defined in claims 1 or 2, wherein said medical device is a stent, graft, valve, screw, nail, rod, PFO device, prosthetic device, sheath, guide wire, balloon catheter, hypotube, catheter, electrophysiology catheter, staple or cutting device.

4. The medical device as defined in claim 2, wherein said metal alloy includes over 99 weight percent of a solid solution.

5. The medical device as defined in claim 2, wherein said metal alloy includes at least about 99.95 weight percent of a solid solution.

6. The medical device as defined in claim 1, wherein said metal alloy has an average density of at least 10 gm/cc.

7. The medical device as defined in claim 4, wherein said metal alloy has an average density of at least 10 gm/cc.

8. The medical device as defined in claim 1, wherein said metal alloy includes about 46-49 weight percent rhenium and about 51-54 weight percent molybdenum.

9. The medical device as defined in claim 7, wherein said metal alloy includes about 46-49 weight percent rhenium and about 51-54 weight percent molybdenum.

10. The medical device as defined in claim 1, wherein said metal alloy includes about 40-50 weight percent rhenium and about 50-60 weight percent molybdenum.

11. The medical device as defined in claim 7, wherein said metal alloy includes about 40-50 weight percent rhenium and about 50-60 weight percent molybdenum.

12. The medical device as defined in claim 4, wherein said metal alloy includes at least about 99.9 weight percent rhenium and molybdenum.

13. The medical device as defined in claim 1, wherein said carbon content of said metal alloy is less than about 100 ppm and said oxygen content of said metal alloy is less than about 50 ppm, and a carbon to oxygen atomic ratio of at least about 2:1.

14. The medical device as defined in claim 8, 9, 10 or 11, wherein said carbon content of said metal alloy is less than about 100 ppm and said oxygen content of said metal alloy is less than about 50 ppm, and a carbon to oxygen atomic ratio of at least about 2:1.

15. The medical device as defined in claim 13, wherein said carbon content of said metal alloy is less than about 50 ppm and said oxygen content of said metal alloy is less than about 10 ppm.

16. The medical device as defined in claim 14, wherein said carbon content of said metal alloy is less than about 50 ppm and said oxygen content of said metal alloy is less than about 10 ppm.

17. The medical device as defined in claim 1, wherein said atomic ratio of carbon to oxygen in said metal alloy is up to about 20:1.

18. The medical device as defined in claim 16, wherein said atomic ratio of carbon to oxygen in said metal alloy is up to about 20:1.

19. The medical device as defined in claim 1, wherein said nitrogen content of said metal alloy is less than about 10 ppm.

20. The medical device as defined in claim 18, wherein said nitrogen content of said metal alloy is less than about 10 ppm.

21. The medical device as defined in claim 1, wherein said metal alloy has an average grain size of about 5-10 ASTM.

22. The medical device as defined in claim 20, wherein said metal alloy has an average grain size of about 5-10 ASTM.

23. The medical device as defined in claim 1, wherein said metal alloy constitutes at least about 80 weight percent of said medical device.

24. The medical device as defined in claim 22, wherein said metal alloy constitutes at least about 80 weight percent of said medical device.

25. The medical device as defined in claim 1, wherein said metal alloy comprises by weight percent:

| | |
|---|---|
| C | <150 ppm |
| Mo | 51-56% |
| O | <50 ppm |
| N | <20 ppm |
| Re | 44-49% | and has an average grain size of about 6-8 ASTM, an average tensile elongation of about 25-35%, and said content of rhenium plus molybdenum is at least about 99.9 weight percent.

26. The medical device as defined in claim 7, wherein said metal alloy comprises by weight percent:

| | |
|---|---|
| C | <150 ppm |
| Mo | 51-56% |
| O | <50 ppm |
| N | <20 ppm |
| Re | 44-49% | and has an average grain size of about 6-8 ASTM, an average tensile elongation of about 25-35%, and said content of rhenium plus molybdenum is at least about 99.9 weight percent.

27. The medical device as defined in claim 1, wherein said metal alloy comprises by weight percent:

| | |
|---|---|
| C | <50 ppm |
| Mo | 52.5-55.5% |
| O | <10 ppm |
| N | <10 ppm |
| Re | 44.5-47.5% | and has an average grain size of about 6-7 ASTM, and an average tensile elongation of about 25-35%, and said content of rhenium plus molybdenum is at least about 99.9 weight percent.

28. The medical device as defined in claim 26, wherein said metal alloy comprises by weight percent:

| | |
|---|---|
| C | <50 ppm |
| Mo | 52.5-55.5% |
| O | <10 ppm |
| N | <10 ppm |
| Re | 44.5-47.5% | and has an average grain size of about 6-7 ASTM, and an average tensile elongation of about 25-35%, and said content of rhenium plus molybdenum is at least about 99.9 weight percent.

29. The medical device as defined in claim 1, wherein said metal alloy comprises by weight percent:

| | |
|---|---|
| C | <50 ppm |
| Mo | 52.5% |
| O | <10 ppm |
| N | <10 ppm |
| Re | 47.5% | and has an average grain size of about 6-7 ASTM, and an average tensile elongation of about 25-35%, and said content of rhenium plus molybdenum is at least about 99.9 weight percent.

30. The medical device as defined in claim 28, wherein said metal alloy comprises by weight percent:

| | |
|---|---|
| C | <50 ppm |
| Mo | 52.5% |
| O | <10 ppm |
| N | <10 ppm |
| Re | 47.5% | and has an average grain size of about 6-7 ASTM, and an average tensile elongation of about 25-35%, and said content of rhenium plus molybdenum is at least about 99.9 weight percent.

31. A stent that is formed of at least about 80 weight percent of a metal alloy which improves the strength and ductility of the stent, said metal alloy including at least about 99.9 weight percent of a solid solution of rhenium and molybdenum, said metal alloy including carbon and oxygen and having a carbon to oxygen atomic ratio of at least about 1:1 and less than about 50:1, said metal alloy having an average yield strength of about 98-122 ksi and an average ultimate tensile strength of about 100-150 ksi, said metal alloy having an average grain size of about 6-9 ASTM, said metal alloy having an average tensile elongation of about 25-35%, and including by weight percent:

| | |
|---|---|
| C | <150 ppm |
| Mo | 51-56% |
| O | <50 ppm |
| N | <20 ppm |
| Re | 44-49%. |

32. The stent as defined in claim 31, wherein said metal alloy comprises by weight percent:

| | |
|---|---|
| C | <50 ppm |
| Mo | 52.5-55.5% |
| O | <10 ppm |
| N | <10 ppm |
| Re | 44.5-47.5% | and an average grain size of about 6-7 ASTM.

33. A medical device at least partially formed of a metal alloy which improves the strength and radiopacity of the medical device, said metal alloy including at least about 95 weight percent of a solid solution of rhenium and molybdenum, said metal alloy including at least 40 weight percent rhenium and at least 40 weight percent molybdenum, said metal alloy including carbon, nitrogen and oxygen, said metal alloy having a nitrogen content of less than about 30 ppm, a carbon content of up to 200 ppm, and an oxygen content of up to 100 ppm, said metal alloy having a carbon to oxygen atomic ratio of at least about 1:1, said metal alloy having a carbon to oxygen atomic ratio of less than about 50:1, said metal alloy having an average yield strength of at least about 70 ksi and an average ultimate tensile strength of about 80-150 ksi, said metal alloy having an average grain size of over 5 ASTM, and said metal alloy having an average tensile elongation of at least about 25%.

* * * * *